US005545622A

United States Patent [19]

Casamassina et al.

[11] Patent Number: 5,545,622

[45] Date of Patent: Aug. 13, 1996

[54] PROCESS FOR PREPARING SURFACTANT MIXTURES HAVING HIGH SOLIDS CONTENT

[75] Inventors: Thomas Casamassina, Totowa; Florencio Morales, Jr., Jersey City; Barry A. Salka, Fair Lawn, all of N.J.; John Fallon, Point Pleasant, Pa.

[73] Assignee: Henkel Corporation, Plymouth Meeting, Pa.

[21] Appl. No.: 120,624

[22] Filed: Sep. 13, 1993

[51] Int. Cl.$^6$ .............................. A61K 31/70; C07G 3/00; C11D 9/00

[52] U.S. Cl. .............................. 252/353; 536/4.1; 514/25; 510/537

[58] Field of Search .............................. 536/124, 4.1, 18.5; 514/25; 252/108, 367, 368, DIG. 1

[56] References Cited

U.S. PATENT DOCUMENTS

| | | | |
|---|---|---|---|
| 4,406,833 | 9/1983 | Boehme et al. | 530/356 |
| 4,857,213 | 8/1989 | Caswell et al. | 252/8.75 |
| 5,073,292 | 12/1991 | Hessel et al. | 252/174.12 |
| 5,174,927 | 12/1992 | Honsa | 252/543 |
| 5,227,086 | 7/1993 | Kacher | 252/108 |
| 5,242,615 | 9/1993 | Urfer et al. | 252/174.17 |
| 5,258,142 | 11/1993 | Giesen et al. | 252/552 |
| 5,266,690 | 11/1993 | McCurry et al. | 536/18.6 |
| 5,308,526 | 5/1994 | Dias et al. | 252/368 |

*Primary Examiner*—Douglas W. Robinson
*Assistant Examiner*—Everett White
*Attorney, Agent, or Firm*—Wayne C. Jaeschke; John E. Drach; Henry E. Millson, Jr.

[57] ABSTRACT

Highly concentrated mixtures of surfactants are obtained by a method which comprises adding the acid form of a neutralizable surfactant to an aqueous composition comprised of a base and an alkyl polyglycoside.

8 Claims, No Drawings

PROCESS FOR PREPARING SURFACTANT MIXTURES HAVING HIGH SOLIDS CONTENT

BACKGROUND OF THE INVENTION

1. Field of the Invention

This invention relates to a process for making surfactant mixtures having a relatively high solids content.

2. Description of the Related Art

Surfactant manufacturers normally seek to prepare their products having as great a solids concentration as possible in order to minimize transportation costs. However, it not always possible to take advantage of such economic benefits when mixtures containing the sodium salts of certain surfactants are being shipped because of the difficulty in preparing such mixtures in highly concentrated form. For example, surfactant mixtures comprised of 25% by weight of the sodium salt of an alcohol sulfate and 25% by weight of an alkyl polyglycoside cannot be made by the conventional method of mixing aqueous solutions of the two components because the water solubility of an alcohol sulfate in water is about 30% by weight while the solubility of a fatty alkyl polyglycoside in water ranges from about 50% to about 65% by weight. Therefore, it would be impossible to make a surfactant mixture containing an alkyl polyglycoside and having 30% by weight of, for example, sodium lauryl sulfate by simply mixing a 30% aqueous sodium lauryl sulfate solution and an aqueous alkyl polyglycoside solution. Such solubility limitations are not encountered with the corresponding ammonium salts of neutralizable surfactants or the sodium or ammonium salts of such surfactants as ethoxylated fatty alcohols. Therefore, mixtures containing high concentrations of such sodium or ammonium salts are obtainable by mixing highly concentrated solutions. In order to minimize the costs of shipping a highly concentrated surfactant mixture, such as one containing sodium lauryl sulfate and an alkyl polyglycoside, a manufacturer would strive to make a surfactant mixture having as little water as possible. The present invention is a method for making a relatively highly concentrated surfactant mixture containing an anionic surfactant and an alkyl polyglycoside regardless of whether or not the anionic surfactant is available itself in a highly concentrated form. The process according to the invention is particularly useful for preparing relatively highly concentrated surfactant mixtures containing the sodium salts of moderately soluble anionic surfactants and alkyl polyglycosides.

SUMMARY OF THE INVENTION

The surprising discovery has been made that highly concentrated mixtures of surfactants can be obtained by a method which comprises adding the acid form of a neutralizable surfactant to an aqueous composition comprised of a base and an alkyl polyglycoside. The concentration of the base in the aqueous composition is such that the pH of the final surfactant mixture has a value of from about 6 to about 8. The method according to the invention affords surfactant mixtures having a total surfactant concentration which cannot be achieved by mixing surfactants in their conventional, commercially available concentrations.

DESCRIPTION OF THE PREFERRED EMBODIMENTS

Other than in the operating examples, or where otherwise indicated, all numbers expressing quantities of ingredients or reaction conditions used herein are to be understood as modified in all instances by the term "about".

The alkyl polyglycosides which can be used in the compositions according to the invention have the formula I $$R_1O(Z)_a \qquad \text{I}$$

wherein $R_1$ is a monovalent organic radical having from about 6 to about 30 carbon atoms; Z is saccharide residue having 5 or 6 carbon atoms; a is a number having a value from 1 to about 6. The alkyl polyglucosides which can be used in the compositions according to the invention have the formula I and are commercially available, for example, as APG®, Glucopon™, or Plantaren™ surfactants from Henkel Corporation, Ambler, Pa., 19002. Examples of such surfactants include but are not limited to:

1. APG® 225—an alkylpolyglycoside in which the alkyl group contains 8 to 10 carbon atoms.
2. APG® 425—an alkyl polyglycoside in which the alkyl group contains 8 to 16 carbon atoms.
3. APG® 625—an alkyl polyglycoside in which the alkyl groups contain 12 to 16 carbon atoms.
4. APG® 300—an alkyl polyglycoside substantially the same as the 325 product above but having a different average degree of polymerization.
5. Glucopon™ 600—an alkylpolyglycoside substantially the same as the 625 product above but having a different average degree of polymerization.
6. Plantaren™ 2000—a $C_{8-16}$ alkyl polyglycoside.
7. Plantaren™ 1300—a $C_{12-16}$ alkyl polyglycoside.
8. Plantaren™ 1200—a $C_{12-16}$ alkyl polyglycoside having an average degree of polymerization of 1.4. Other examples include alkyl polyglycoside surfactant compositions which are comprised of mixtures of compounds of formula I wherein Z represents a moiety derived from a reducing saccharide containing 5 or 6 carbon atoms; a is zero; b is a number from 1.8 to 3; and $R^1$ is an alkyl radical having from 8 to 20 carbon atoms. The composition is characterized in that it has increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and poly-glycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in copending application Ser. No. 07/810,588, filed on Dec. 19, 1991, (now U.S. Pat. No. 5,266,690) the entire contents of which are incorporated herein by reference.

The neutralizable surfactants which can be used in the process according to the invention can be any surfactant which can exist in an acid form and subsequently converted to the anionic form through neutralization with a base. Examples of such surfactants include, but are not limited to, the acid form of alkyl isethionates, alkyl sarcosonates, sulfosuccinates, alkyl ether sulfates, alkyl sulfates, alkyl taurates, and olefin sulfonates. Another type of neutralizable surfactant is a protein condensate which is the reaction product of a hydrolyzed protein and a fatty acid chloride. An example of a hydrolyzed protein is a hydrolyzed collagen which is commercially available as, for example, Nutrilan® I or Nutrilan® L, each of which is a trademark product of Henkel Corporation, Ambler, PA. An example of a preferred protein condensate is the reaction product of a hydrolyzed collagen having a molecular weight of 500 Daltons and coco fatty acid chloride.

The base which can be used in the process according to the invention is any water soluble base which is deemed suitable for the neutralization of the sauer ester. Such bases include alkali metal hydroxides such as sodium and potassium hydroxide used either in the solid form or as an aqueous solution such as a 50% aqueous solution of sodium hydroxide which is a preferred form of sodium hydroxide. The base can also be a water soluble amine such as ammonia or a water soluble primary, secondary, or tertiary amine or a water soluble polyamine such as ethylene diamine or diethylenetriamine. When the process according to the invention is used to prepare the sodium salt of a moderately soluble anionic surfactant such as sodium lauryl sulfate, the base will obviously be sodium hydroxide. Sodium hydroxide is an especially preferred base because the process according to the invention is particularly useful for preparing relatively highly concentrated surfactant mixtures containing the sodium salts of moderately soluble anionic surfactants and alkyl polyglycosides which are not otherwise obtainable by mixing solutions of the individual surfactants.

Other materials which may be used in the process according to the invention include polyethylene oxide which can be added to remove haze from the final product made by the process according to the invention. Polyethylene oxide polymers having a molecular weight in the range of from 200 to 1,000 are preferred and are commercially available, for example, from Union Carbide Corp. as Carbowax® polymers such as Carbowax® 700. Preferably, 1–3% by weight polyethylene oxide is added to the clarify the neutralization mix.

The process according to the invention may be carried out in any convenient manner in any type of vessel. The acid form of the neutralizable surfactant is added to an aqueous composition which is comprised of a base and an alkyl polyglycoside while the neutralization mixture is vigorously agitated to avoid lump formation. The concentration of the base in the aqueous composition is such that the pH of the final surfactant mixture has a value of from about 6 to about 8.

The process according to the invention results in compositions comprised of: (a) water, (b) from about 25% to about 40% by weight of the sodium salt an anionic surfactant selected from the group consisting of: (i) an alkyl isethionate, (ii) an alkyl sarcosonate, (iii) a sulfosuccinate, (iv) an alkyl sulfate, (v) an alkyl taurate, (vi) an olefin sulfonate, or a mixture comprised of any two or more of surfactants (i)-(vi) and, (c) from about 25% to about 40% by weight of an alkyl polyglycoside of the formula I as defined above.

The following examples are meant to illustrate but not limit the invention.

EXAMPLE 1

Into a 2000 ml, 4-neck flask were placed 190 grams (1.0 mole) of a $C_{12-14}$ fatty alcohol. The flask was immersed in an ice bath to cool the contents and placed under vacuum by means of a water aspirator. When the temperature of the fatty alcohol reached 20° C., 116.5 grams (1.0 mole) of chlorosulfonic acid was added from a dropping funnel having a delivery tube long enough to extend below the fatty alcohol surface. The chlorosulfonic acid was added at such a rate as to maintain a reaction temperature in the 20° C.–35° C. range. After the addition of the chlorosulfonic acid had been completed, the reaction mixture was stripped under full vacuum for 30 minutes to yield sauer ester.

About 240 grams of the sauer ester were placed in an addition funnel and were added to 760 grams of a neutralization mix comprised of 55 grams of 50% aqueous NaOH, 200 grams of Plantaren™ 2000, 300 grams of Plantaren™ 1300, 15 grams of Carbowax 400, 160 grams of water, 10 grams of sodium citrate, and 20 grams of KCl. The sauer ester was added to the neutralization mix with vigorous stirring and at a rate which avoided lump formation. The temperature rose to >45° C. The pH was monitored so that it did not fall to the acid side. In the event that the pH did drop below 7.0, sufficient 50% aqueous NaOH was added to restore the pH to an alkaline value. After all the sauer ester was added and the neutralized sauer ester completely dissolved, a sodium citrate buffer was added to bring the pH to a value of 6.0–7.0. The resulting solution contained 25% by weight of neutralized fatty alcohol sulfonate and 25% total of alkyl polyglycoside (a combination of Plantaren™ 1300 & 2000) for a total surfactant solids concentration equal to 50% by weight.

EXAMPLE 2

About 35 grams of protein-fatty acid condensate were placed in an addition funnel and were added to a neutralization mix comprised of 7.9 grams of water, 0.5 grams of Carbowax® 400, 6.6 grams of 45% aqueous KOH, and 50 grams of Plantaren™ 2000. The protein-fatty acid condensate was added to the neutralization mix with vigorous stirring and at a rate which avoided lump formation. The temperature rose to >45° C. The pH was monitored so that it did not fall to the acid side. In the event that the pH did drop below 7.0, sufficient 50% aqueous NaOH was added to restore the pH to an alkaline value. An additional 0.5 grams of Carbowax® 400 was added to clear the final product solution, which is the sodium salt of the neutralized protein-fatty acid condensate, had a Brookfield (LVT, spindle #3, @12 rpm) viscosity of 4400 cps at 25° C. and a total solids of 51%. The pH at 10% solids was 7.99.

What is claimed is:

1. A composition consisting essentially of: (a) water, (b) from about 25% to about 40% by weight of the sodium salt of an anionic surfactant selected from the group consisting of: an alkyl isethionate, an alkyl sarcosinate, a sulfosuccinate, an alkyl taurate, an olefin sulfonate, and a mixture thereof and, (c) from about 25% to about 40% by weight of a compound of the formula $$R_1O(Z)_a \qquad I$$

wherein $R_1$ is a monovalent organic radical having from about 6 to about 30 carbon atoms; Z is a saccharide residue having 5 or 6 carbon atoms; a is a number having a value from 1 to about 6, wherein the composition is in the form of a concentrated solution.

2. The composition of claim 1 wherein said compound of formula I is a $C_{8-16}$ alkyl polyglycoside.

3. The composition of claim 1 wherein said compound of formula I is a $C_{12-16}$ alkyl polyglycoside.

4. The composition of claim 1 wherein said compound of formula I is a $C_{12-16}$ alkyl polyglycoside having an average degree of polymerization of 1.4.

5. A composition consisting essentially of: (a) water, (b) from about 25% to about 40% by weight of the sodium salt of a neutralized protein-fatty acid condensate and, (c) from about 25 % to about 40% by weight of a $C_{8-16}$ alkyl polyglycoside, wherein the composition is in the form of a concentrated solution.

6. A composition consisting essentially of: (a) water, (b) from about 25% to about 40% by weight of the sodium salt of a neutralized protein-fatty acid condensate and, (c) from about 25% to about 40% by weight of a $C_{12-16}$ alkyl polyglycoside, wherein the composition is in the form of a concentrated solution.

7. A composition consisting essentially of: (a) water, (b) from about 25 % to about 40% by weight of the sodium salt of the neutralized protein-fatty acid condensate and, (c) from about 25% to about 40% by weight of a $C_{12-16}$ alkyl polyglycoside having an average degree of polymerization of 1.4, wherein the composition is in the form of a concentrated solution.

8. A composition consisting essentially of: (a) water, (b) from about 25% to about 40% by weight of the sodium salt of a neutralized protein-fatty acid condensate and, (c) from about 25 % to about 40% by weight of a mixture comprising a $C_{8-16}$ alkyl polyglycoside and a $C_{12-16}$ alkyl polyglycoside, wherein the composition is in the form of a concentrated solution.

* * * * *